United States Patent
Kim et al.

(10) Patent No.: US 8,546,116 B2
(45) Date of Patent: Oct. 1, 2013

(54) METHOD FOR FRACTIONATING LIGNOCELLULOSE-BASED BIOMASS

(75) Inventors: Jin Woo Kim, Bucheon-si (KR); Jae Chan Park, Yongin-si (KR); Hwa Young Cho, Hwaseong-si (KR); Jun Seok Kim, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 207 days.

(21) Appl. No.: 12/538,538

(22) Filed: Aug. 10, 2009

(65) Prior Publication Data

US 2010/0203605 A1    Aug. 12, 2010

(30) Foreign Application Priority Data

Oct. 29, 2008 (KR) .................. 10-2008-0106618
Jul. 2, 2009 (KR) .................. 10-2009-0060397

(51) Int. Cl.
*C12P 7/06* (2006.01)
(52) U.S. Cl.
USPC ....................................................... 435/161
(58) Field of Classification Search
USPC ................................................. 530/500–507
See application file for complete search history.

(56) References Cited

U.S. PATENT DOCUMENTS

| | | | | |
|---|---|---|---|---|
| 3,954,497 A | * | 5/1976 | Friese | 127/37 |
| 4,072,538 A | * | 2/1978 | Fahn et al. | 127/37 |
| 5,358,646 A | | 10/1994 | Gloyna et al. | |
| 2008/0029233 A1 | | 2/2008 | Wingerson et al. | |

FOREIGN PATENT DOCUMENTS

| | | |
|---|---|---|
| CA | 2 529 228 | 6/2007 |
| JP | 2007-202518 | 8/2007 |
| WO | 2007111605 | 10/2007 |

* cited by examiner

*Primary Examiner* — Jon P Weber
*Assistant Examiner* — Robert Yamasaki
(74) *Attorney, Agent, or Firm* — Leydig, Voit & Mayer, Ltd.

(57) ABSTRACT

A method and apparatus for fractionating a lignocellulose-based biomass are provided. The method includes providing a lignocellulose-based biomass, extracting lignin from the biomass by adding a first solvent capable of dissolving the lignin, extracting xylose by adding a second solvent capable of dissolving hemicellulose to the biomass treated with the first solvent, and extracting the cellulose remaining in the biomass. In this method, a continuous process can be performed instead of a low efficiency batch-type process and components of the biomass can be obtained at high yield.

10 Claims, 4 Drawing Sheets

METHOD FOR FRACTIONATING LIGNOCELLULOSE-BASED BIOMASS

CROSS-REFERENCE TO RELATED APPLICATION

This application claims the benefit of Korean Patent Application No. 10-2008-0106618, filed on Oct. 29, 2008, and Korean Patent Application No. 10-2009-0060397, filed on Jul. 2, 2009 and all the benefits accruing therefrom under 35 U.S.C. §119 which is hereby incorporated by reference as if fully set forth herein.

BACKGROUND

1. Field

The disclosure relates to a method and apparatus for fractionating a lignocellulose-based biomass.

2. Description of the Related Art

With globally increasing concern about exhaustion of resources and pollution of the environment by overuse of fossil fuels, new and renewable substitute energy resources for stably and continuously producing energy are being considered. In the ongoing development of such substitute energy resources, a technique of producing alcohol from biomass is receiving considerable attention.

The most abundant and fully renewable biomass on the planet is lignocellulose. Lignocellulose is a complex structure of a non-biodegradable aromatic polymer such as lignin, and carbohydrates such as cellulose and hemicellulose. The lignocellulose has often been used to refer to biomass. Various water-soluble fuels such as alcohol, diesel, and hydrogen, which are produced from biomass, are generally called bioenergy.

Cellulose, a significant component of lignocellulose, is a stable polysaccharide consisting of a linear chain of glucose units joined by β-1,4 glycosidic bonds, making it far more physically and chemically robust than a helical amylose consisting of glucose units joined by α-1,4 glycosidic bonds in the natural state.

Hemicellulose, another significant component of lignocellulose, is a polysaccharide with a lower degree of polymerization than cellulose. Hemicellulose consists of a polymer of pentose such as xylose as a main component and lesser amounts of a polymer of pentose such as arabinose and a polymer of hexose such as mannose, galactose or glucose. Because hemicellulose has a lower degree of polymerization and has a less regular structure than cellulose, it is more easily degraded by physical and chemical treatments.

Lignin is a hydrophobic macromolecular polymer with a complex structure. Lignin, in part, contributes to the protection of plants from various biochemical threats posed by insects and microorganisms such as mold. Because lignin is highly durable both physically and chemically, it is regarded as one of the most non-degradable compounds in nature.

In order to produce ethanol or various compounds from lignocellulose, polysaccharides forming the lignocellulose must be converted into fermentable sugars (sugar platforms) capable of ethanol fermentation. Liquid fuels such as ethanol and butanol, organic acids which are monomers of biopolymers such as polylactic acids, and various amino acids are producible from the fermentable sugars. The concept of the sugar platform was initially conceived by the U.S. Department of Energy (DOE). Here, conversion of lignocellulose into a sugar platform involves pretreating or fractionating the lignocellulose to produce sugars from cellulose and hemicellulose.

The pretreatment of the lignocellulose can be largely classified into physical, chemical, and biological methods.

Physical methods can include a milling process and a steam explosion process. The milling process includes crushing lignocellulose particles into small-size particles using a milling machine, thereby causing a structural change to the lignocellulose. The milling process is not frequently used because it consumes a considerable amount of energy and offers a low yield or a low saccharification. The steam explosion process includes steaming lignocellulose for a predetermined time in a high-pressure container of hot steam and opening a valve of the container instantaneously to allow the structure of the lignocellulose to be more accessible to enzymatic attack.

In order to increase the effects of the above-described physical methods, much research has been conducted on combinations of chemical and physical methods. A typical example of a combination of chemical and physical methods is a dilute-acid hydrolysis process. This process involves dipping lignocellulose in a 2% (w/w) or less solution of sulfuric acid and steaming the lignocellulose in a container of hot vapor for about 60 seconds to about 10 minutes at a temperature of about 160 to about 200° C. similarly to the steam explosion process. In this process, hemicellulose is hydrolyzed into monosaccharides and oligo-saccharides by acid catalysis and some pentose that is produced can be degraded into furfural by excessive reaction, which can act as a fermentation-inhibitor.

In the dilute-acid hydrolysis process, the hemicellulose is hydrolyzed to break bonds between the cellulose and the hemicellulose and between lignin and the hemicellulose, thereby facilitating enzymatic saccharification. Accordingly, a hemicellulose hydrolysate, such as xylose, which is hydrolyzed and dissolved in a hydrolyzate, can be obtained and separated during the fractionation process. Subsequently, both insoluble cellulose and lignin, which were not degraded during the fractionation process, are subjected to enzymatic saccharification, and then converted into glucose and lignin residues, so that the lignin can be transferred together to a subsequent fermentation process. In this case, however, phenolic compounds derived from the lignin degradation can inhibit the enzymatic process and the fermentation process.

An alternate method of fractionating a biomass using a base instead of an acid is the ammonia fiber explosion (AFEX) process developed by Bruce Dale et al. ("Enzyme hydrolysis and ethanol fermentation of liquid hot water and AFEX pretreated distillers' grains at high-solids loadings" *Bioresource Technology*, Volume 99, Issue 12, August 2008, Pages 5206-5215. Youngmi Kim, Rick Hendrickson, Nathan S. Mosier, Michael R. Ladisch, Bryan Bals, Venkatesh Balan, Bruce E. Dale). According to the AFEX process, ammonia and a biomass are mixed in a ratio of 1:1 to 1:3, the resulting mixture is treated at a high temperature for about 5 to about 30 minutes, and the pressure of a reaction vessel containing the mixture is explosively released to atmospheric pressure to retrieve gaseous ammonia and cause physical and chemical changes to the biomass structure, thereby improving the rate of enzymatic saccharification. In this process, little hemicellulose is hydrolyzed, but most lignin is dissolved and separated from cellulose and hemicellulose so that the cellulose and the hemicellulose can be saccharized during a subsequent enzymatic saccharification process to obtain glucose and pentose such as xylose.

A biological-based fractionation process can include pretreatment principally using mold, for example, white-rot fungus, which grow using saccharides obtained by degrading lignocellulose, under mild conditions. However, while the biological fractionation process is quite efficient, its productivity is relatively low and the enzyme is expensive so that it has not been put to large scale commercial and only used in small scale production.

SUMMARY

Exemplary embodiments provide a method and apparatus for continuously fractionating a lignocellulose-based biomass using two solvents, wherein lignin is primarily extracted using a first solvent and xylose is secondarily extracted using a second solvent.

A structure of lignocellulose is shown in FIG. 1. Lignin is joined to hemicellulose by covalent bonds, and the hemicellulose is joined to cellulose by hydrogen bonds. On the whole, the hemicellulose surrounds a linear cellulose microfibril by hydrogen bonds and is surrounded by the lignin by covalent bonds. That is, the lignocellulose is structured to protect the cellulose, i.e., a main carbohydrate of plants.

In pretreating process, as shown in FIG. 2, the lignin and the hemicellulose are partially removed from the lignocellulose or the bonds between the hemicellulose and the cellulose are loosened, and the cellulose is also partially degraded, so that cellulase can more easily interact with the cellulose.

An exemplary embodiment provides a method of fractioning lignocellulose by components by pretreatment. According to the exemplary embodiment, a method of fractionating a lignocellulose-based biomass includes: providing the lignocellulose-based biomass (hereinafter, sometimes referred to as 'biomass providing process'); extracting lignin from the biomass by adding a first solvent capable of dissolving the lignin (hereinafter, sometimes referred to as 'lignin extraction process'); extracting xylose by adding a second solvent capable of dissolving hemicellulose to the biomass treated with the first solvent during the lignin extraction process (hereinafter, sometimes referred to as 'xylose extraction process'); and extracting the remaining cellulose from the biomass, from which the lignin and the xylose are extracted, treated with the second solvent (hereinafter, sometimes referred to as 'cellulose extraction process').

The method can be continuously performed in a single reaction vessel to extract the lignin, the xylose, and the cellulose sequentially, thereby improving process efficiency.

According to another exemplary embodiment, a method of fractionating a lignocellulose-based biomass includes: providing the lignocellulose-based biomass; extracting lignin from the biomass by adding aqueous ammonia or a basic solvent into a reaction vessel and capturing the lignin in a first storage tank; extracting xylose from the biomass treated with the aqueous ammonia or the basic solvent by adding an acidic solvent into the reaction vessel and capturing the xylose in a second storage tank; and extracting the remaining cellulose from the biomass, a solid component contained in the reaction vessel. In this method, the lignin, xylose, and cellulose can be extracted in a single reaction vessel.

The reaction vessel can be maintained at a temperature of about 80 to about 150° C. under a pressure of about 50 to about 330 psig or about 250 to about 300 psig.

According to still another exemplary embodiment, a method of producing biofuel such as bioalcohol from the cellulose or xylose extracted using the above-described methods is provided. For example, the cellulose can be extracted from the biomass from which the lignin and the xylose are extracted, hydrolyzed and fermented to produce ethanol, and the xylose can also be fermented to produce ethanol. The hydrolysis of the cellulose can be performed using an enzymatic saccharification process.

According to yet another exemplary embodiment, an apparatus for fractionating the lignocellulose-based biomass is provided. The apparatus includes: a reaction vessel configured to contain a biomass; first and second solvent tanks equipped at one side of the reaction vessel and configured to contain first and second solvents to be added to the reaction vessel, where the first solvent tank contains a first solvent and the second solvent tank contains a second solvent; and first and second storage tanks equipped at the other side of the reaction vessel and configured to store extracts from the reaction vessel, where the first storage tank stores lignin and the second storage tank stores xylose.

The fractionation apparatus can further include a third solvent tank configured to contain water. The first solvent can be aqueous ammonia or a basic solvent, and the second solvent can be an acidic solvent. For example, the basic solvent can include NaOH, and the acidic solvent can include $H_2SO_4$.

A solvent pump can be further provided between the reaction vessel and the first and second solvent tanks. Also, a pre-heater and/or a steam generator can be further provided between the solvent pump and the reaction vessel.

In addition, a cooler and/or a heat exchanger can be further provided between the reaction vessel and the first and second storage tanks, and a pressurizer can be coupled to the first and second storage tanks.

In order to maintain pressure throughout the apparatus described above, a back pressure regulator can be installed between the reaction vessel and the first and second storage tanks, or a pressure regulator configured to inject compressed nitrogen to maintain a pressure of about 50 to about 330 psig can be coupled to the pressurizer.

In some cases, the fractionation apparatus can further include a third storage tank configured to store glucose.

BRIEF DESCRIPTION OF THE DRAWINGS

Exemplary embodiments are described in further detail below with reference to the accompanying drawings. It should be understood that various aspects of the drawings may have been exaggerated for clarity.

DETAILED DESCRIPTION

Figure 1:
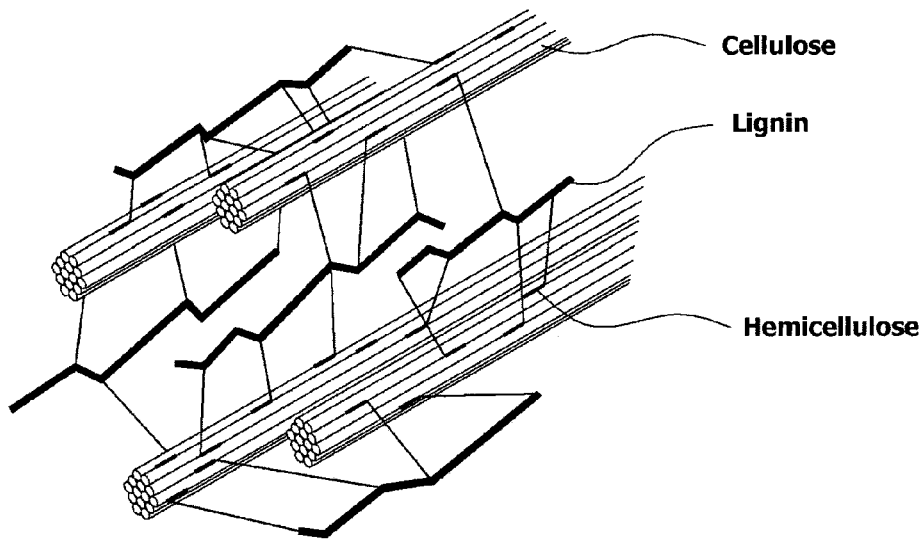
FIG. 1 is a schematic diagram of the structure of lignocellulose.
Figure 2:
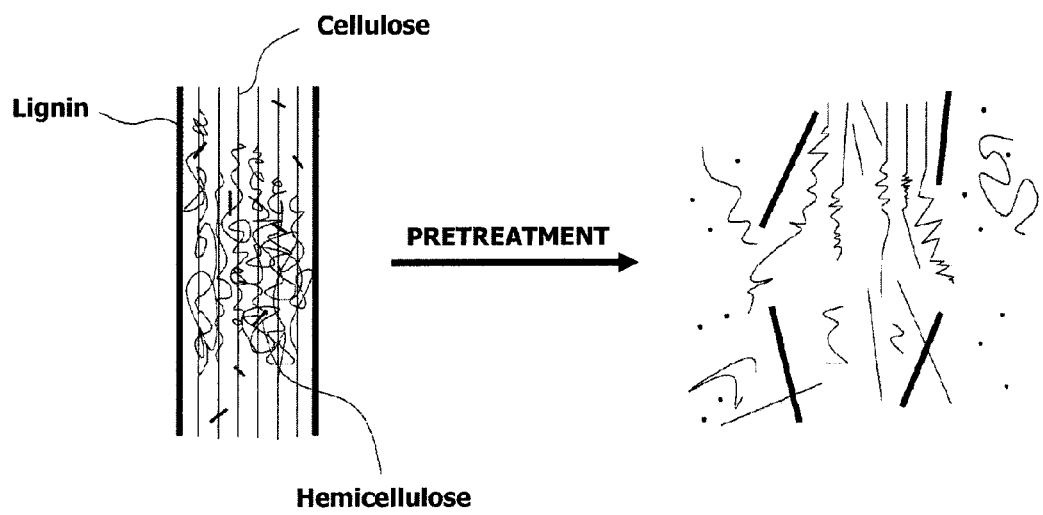
FIG. 2 is a schematic diagram showing a structural change of lignocellulose during a pretreatment (or fractionation) process.

Various exemplary embodiments will now be described more fully with reference to the accompanying drawings in which some exemplary embodiments are shown. In the drawings, the thicknesses of layers and regions may be exaggerated for clarity.

1. A Method of Fractionating a Lignocellulose-Based Biomass

Figure 3:
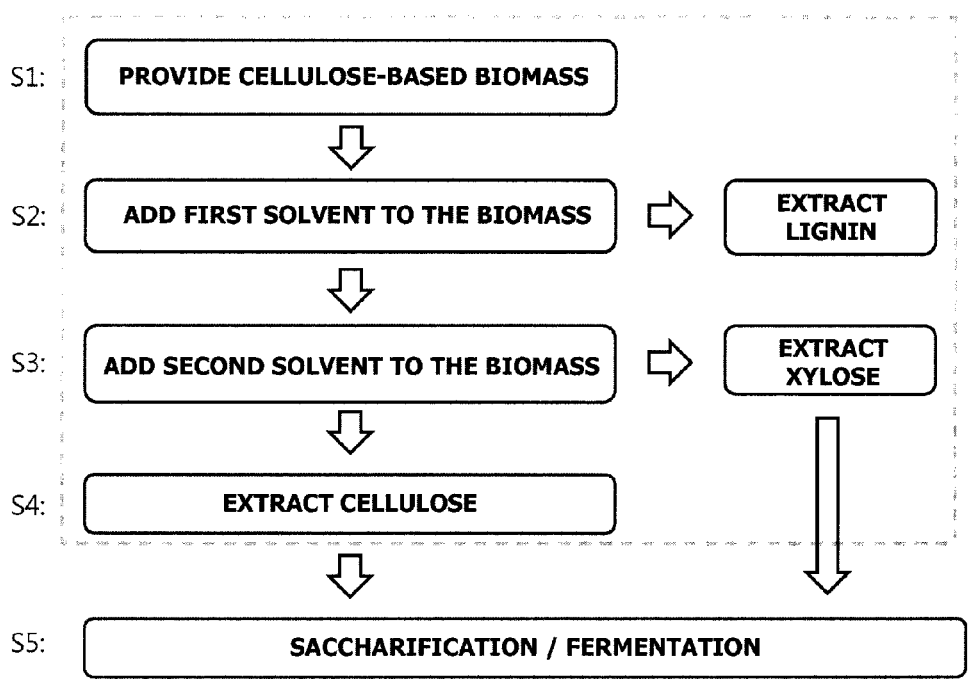
FIG. 3 is a flowchart of a fractionation process according to an exemplary embodiment.

FIG. 3 is a flowchart of a method of fractionating a lignocellulose-based biomass according to an exemplary embodiment.

Referring to FIG. 3, the method of fractionating a lignocellulose-based biomass can include: providing the lignocellulose-based biomass (operation S1); extracting lignin from the biomass by adding a first solvent for dissolving the lignin (operation S2); extracting xylose from the biomass processed with the first solvent in the lignin extraction process by adding a second solvent for dissolving at least a portion of hemicellulose to the reaction vessel (operation S3); and extracting the remaining cellulose from the biomass (operation S4).

According to the method shown in FIG. 3, the lignocellulose-based biomass can be continuously processed in a single reaction vessel, where not only the cellulose, a main component of the lignocellulose-based biomass, but also the lignin and the xylose can be fractionated simultaneously in the reaction vessel. Accordingly, the fractionation process according to the exemplary embodiment has excellent process efficiency compared to a conventional batch-type discontinuous fractionation process using a plurality of reaction vessels to extract other components from extracts after extracting individual components of the lignocellulose-based biomass.

Also, a saccharification process of the extracted cellulose into a fermentable saccharide or a fermentation process can be performed immediately after the fractionation process is finished, thereby reducing process costs. In particular, xylose is extracted as a saccharified sugar in the form of a monosaccharide that does not need enzymatic saccharification and the monosaccharide has a suitable pH for fermentation, e.g., approximately pH 6, so that it can be directly utilized in the fermentation process.

Furthermore, according to the method of the exemplary embodiment, extracting the lignin from the biomass can be followed by extracting the xylose from the hemicellulose, so that the fractionation process can be performed under relatively mild conditions. Accordingly, the generation of materials capable of inhibiting saccharification and fermentation such as furfural can be minimized, and the yield and production of the xylose can be unexpectedly increased. As a result, the amount of enzyme used, which takes up a large portion of the cost of production of biofuel by saccharification of cellulose, can be significantly reduced, and a reaction rate can be increased, thereby increasing saccharification yield.

For reference, in the lignin extraction process, hemicellulose extraction process, and cellulose extraction process, main extracts are lignin, hemicellulose and cellulose, respectively. For example, while, in the lignin extraction process, lignin and hemicellulose can be extracted together, the content of lignin is relatively higher than those of other extracts. Accordingly, the extracts from these processes include, but not limited to, lignin, hemicellulose, cellulose and combinations thereof.

In the lignin extraction process, the lignocellulose-based biomass can be provided, for example, in the form of a pellet or chip. The lignocellulose-based biomass can be formed of hard wood, soft wood, herbaceous plants, recycled paper, waste paper, wood chips, pulp, paper waste, wood waste, thinning-out trees, cornstalks, corncobs, rice straws, chaff, wheat straws, sugarcane cobs, palm tree by-products, bagasse, agricultural byproducts and waste, livestock manure, or a combination thereof, but not limited thereto.

The biomass can be supplied continuously or discontinuously without any limitation.

Also, the biomass can be supplied discontinuously when respective processes are discontinuously performed. For example, after the reaction vessel is filled with the biomass, respective components are extracted according to the above-described fractionation method, the biomass, a solid component remaining in the reaction vessel, is removed, and then the reaction vessel is filled with another biomass.

When the biomass can be supplied continuously, for example, a biomass supplier, a reaction vessel, and a biomass discharger are integrally constructed. In this case, after components are extracted from the biomass, another biomass can be supplied from the biomass supplier at the same time as solid components are being transferred from the reaction vessel to the separator.

Here, the reaction vessel can be a percolation device or an extruder, but not limited thereto.

If the biomass is fractionated at an excessively high temperature, hemicellulose is excessively degraded into furfural or cellulose is excessively degraded into hydroxyl furfural, resulting in a lower yield of xylose. For example, because a conventional fractionation process such as a steam explosion process is performed at a high temperature of about 180 to about 250° C. under a high pressure after an acidic catalyst is added, a large amount of energy is required and hemicellulose cannot be substantially used.

However, according to the exemplary embodiments, lignin, a non-degradable component, is primarily extracted from the biomass to facilitate retrieval of xylose from hemicellulose, and thus the remaining fractionation process can be performed under relatively mild conditions.

For example, the reaction vessel can be maintained at a temperature of about 50 to about 200° C., about 80 to about 150° C., about 90 to about 180° C., about 100 to about 150° C., or about 120 to about 160° C. in the fractionation process. In some cases, a reaction temperature even can be lowered to about 50° C. by extending the soak time. In order to maintain a solid-liquid reaction, the reaction vessel can be maintained at a pressure of about 50 to about 330 psig, about 130 to about 320 psig, about 140 to about 300 psig, about 150 to about 300 psig, or about 250 to about 300 psig. Thus, excessive degradation of the hemicellulose can be prevented, thereby greatly improving the yield rate and availability of xylose.

In order to increase the reactivity of the biomass in the reaction vessel, vapor can be supplied from a vapor supplier, such as a steam generator, the reaction vessel can be pre-heated using a preheating coil, and the first and second solvents can be pre-heated before they supplied to the reaction vessel in operations S2 and S3, if desired.

The above-described reaction conditions can be continuously maintained during the entire fractionation process. The pressure condition can be maintained by installing a back pressure regulator between the reaction vessel and the storage tank or injecting compressed nitrogen or compressed air into a pressurizer.

In operation S2, lignin is extracted by adding a first solvent to the biomass, wherein the first solvent can be a solvent capable of dissolving at least a portion of lignin, for example, about 50% or about 65% or more lignin. However, under the given conditions, a solvent excessively dissolving cellulose and hemicellulose is not appropriate.

In one example, the first solvent for extracting the lignin can be aqueous ammonia or a basic solvent having a pH of 10 or more, which can percolate the lignin. The basic solvent can range from about pH 10 to about pH 13. For instance, the first solvent can be at least one selected from the group consisting of sodium hydroxide (NaOH), calcium hydroxide ($Ca(OH)_2$), sodium sulfide ($Na_2S$), potassium hydroxide (KOH) and combinations thereof.

Although the concentration of the first solvent is not specifically limited, supply of the first solvent with a high concentration can lead to an increase in the cost of raw materials and process instability due to a high steam pressure, an increase in the cost of retrieval, corrosion of devices, and environmental pollution etc. Accordingly, the aqueous ammonia can be supplied at a concentration of about 1 to about 30 wt % or about 3 to about 20 wt % based on the total weight of the solvent and the basic solvent can be supplied at a concentration of about 1 to about 30 wt % or about 2 to about 15% based on the total weight of the solvent.

Also, the first solvent can stay in the reaction vessel for about 1 minute to about 1 hour, or about 5 to about 40 minutes.

As described above, the lignin can be extracted from the biomass by adding the first solvent into the reaction vessel. The extracted lignin can be transferred to a first storage tank. In order to increase the retrieval rate, the extracted lignin can be transferred after it is subjected to a cooling process or a heat exchange process.

In operation S2, the yield of the extracted lignin can be at least about 30%, about 40%, about 50%, about 60%, or about 65% in order to minimize the inhibitory reaction in the enzymatic saccharification process.

The lignin is a hydrophobic macromolecular polymer with a complicated structure, which contains large amounts of aromatic compounds formed by polymerization of methoxylated p-coumaryl alcohol, coniferyl alcohol, or sinapyl alcohol. Accordingly, the extracted lignin can be used as fuel for steam boilers or power plant boilers or used as phenolic chemicals by being degraded, without any additional treatment.

The first solvent can be distilled and recycled after the lignin is extracted.

As described above, in the exemplary embodiments, lignin, which is an insoluble main component of the lignocellulose forming the lignocellulose-based biomass, is primarily extracted so that xylose can be extracted under relatively mild conditions.

For example, in order to maximize delignification and the yield rate of xylose, a process temperature can be varied between operations S2 and S3, that is, at a point in time where the second solvent is injected. The process temperature can be optimized considering the delignification effect of the biomass and the yield of xylose. This temperature can be, for example, about 80° C. to about 15° C.

In operation S3, the hemicellulose is extracted by adding a second solvent to the biomass from which at least a portion of the lignin is extracted.

The second solvent is capable of dissolving at least a portion of the hemicellulose, for example, at least about 50%, about 60%, about 70% or about 80% of the hemicellulose.

The second solvent can be an acidic solvent having pH 6.5 or less. For example, the second solvent can be at least one selected from the group consisting of sulfuric acid ($H_2SO_4$), hydrochloric acid (HCl), phosphoric acid ($H_3PO_4$), nitric acid ($HNO_3$), acetic acid ($CH_3COOH$), peracidic acid (peroxyacetic acid (PAA)) and combinations thereof.

The second solvent can have a concentration of about 0.1 to about 10 wt %, about 0.5 to about 5 wt % or about 0.5 to about 3 wt % based on the total weight of the solvent.

In operation (3), when the second solvent is added, a pentose polymer forming hemicellulose is degraded into monosaccharides. When the reaction temperature is too high and pH is too low, the monosaccharides are excessively degraded and converted into a fermentation by-product such as furfural.

Contrarily, when the reaction temperature is too low and pH is in a neutral or basic level, the hemicellulose cannot be degraded into pentose monosaccharides, and be present in the form of oligomers.

In order to prevent production of the by-product such as furfural as well as increase the content of the extracted monosaccharides, the reaction temperature can range from about 50 to about 200° C. or about 100 to about 150° C., and the biomass remaining after operation (3) can be adjusted to pH 4 to 7 or pH 4 to 6.

In this range of pH, effective enzyme activity can be obtained, so that the extracted xylose and the remaining cellulose can be directly utilized in the saccharification or fermentation process without a separate neutralization or pH adjustment process.

Since long process time can also stimulate the production of the fermentation by-product such as furfural, process time to each solvent can be about 10 to 20 minutes.

For example, the first solvent can be aqueous ammonia or a basic solvent, and the second solvent can be an acidic solvent. In this case, the pH in the reaction vessel can be adjusted to be acidic or neutral by injection of the second solvent.

Aqueous ammonia or a basic solvent can be used as the first solvent and an acidic solvent can be used as the second solvent. In this case, the pH of the reaction vessel can be adjusted to acidic or neutral by the addition of the second solvent.

Here, since the biomass treated with the solvent is basic, a large amount of acidic solvent has to be added for a long time to adjust the pH of the reaction vessel to about 4 to about 7 by the addition of the second solvent.

In one example, after the lignin is extracted, the biomass can be subjected to a washing process. The washing process can be performed by opening an outlet of the reaction vessel under high pressure to remove a base after the extraction of the lignin, and adding water 1 to 3 times higher in volume than the reaction vessel at a temperature of about 100° C. or less.

According to this washing process, lignin or base remaining in the reaction vessel can be removed. Also, the amount of the second solvent such as an acid solvent, used in the extraction process of the xylose, can be reduced.

In another example, the xylose extraction process can be performed by adding an acid with a high concentration of about 3 to 8 wt % based on the total weight of the solvent for about 1 to 10 minutes, and adding an acid with a low concentration of about 0.1 to about 3 wt % based on the total weight of the solvent for about 10 to 30 minutes, without using a washing process.

For example, by adding an acid with a high concentration of about 5 wt %, the biomass can be neutralized, and then an acid with a concentration of about 1 to about 2 wt %, which is suitable for retrieval of pentose, can be added, so that the retrieval rate of pentose can be raised, and generation of fermentation by-products can be greatly reduced.

As described above, the extracted lignin and xylose can be transferred to storage tanks, respectively. For example, the extracted lignin and xylose can be subjected to a cooling process or a heat exchange process before transferring to the storage tanks.

That is, in operation S3, by adding the second solvent into the reaction vessel, xylose, a component of the hemicellulose, can be extracted from the biomass. In order to minimize excessive degradation of the extracted xylose, the xylose, separated from the lignin, can be subjected to a cooling or heat exchange process before transferring to a second storage tank. This heat exchange process can prevent excessive degradation of xylose, a monosaccharide, due to heat.

Since the xylose is extracted in operation S3 under relatively mild conditions, excessive degradation of xylose into furfural is minimized, thereby greatly increasing the yield of xylose. Also, the extracted xylose can be directly applied to the fermentation process without additional cleaning and neutralization processes. However, the cleaning processes and neutralization processes can be performed before the fermentation process, if desired.

Concentrations of the pentose and hexose contained in the liquid extract in operation S3 can be about 5 to about 10 wt % and about 1 to about 3 wt %, respectively. The yield of xylose finally extracted can be at least about 70 wt %, about 75 wt %, about 80 wt % or about 85 wt %. There is currently no known technique capable of extracting xylose at such a high yield without producing or removing the fermentation by-product.

Meanwhile, conventionally xylose is separated by a single process using only diluted sulfuric acid. Because lignin structurally surrounds and protects hemicellulose, the hemicellulose cannot be effectively degraded. Accordingly, in order to facilitate delignification and separation of the hemicellulose, it is necessary to raise the process temperature, extend the process time, or increase the concentration of the sulfuric acid. However, this conventional process leads to the formation of fermentation-inhibitors such as furfural because of the more severe reaction conditions. Because of the increase in the amount of acid used, more neutralizer is used which raises costs. As a result, the extracted xylose can have a sugar concentration of about 0.5 wt % or less, which makes it difficult to be utilized in a fermentation process which often uses higher sugar concentrations.

In contrast, xylose extracted according to the method of the exemplary embodiments is possible to extract a very high concentration of sugar from the xylose. The average sugar concentration can be about 2.0 to about 15 wt %, or about 3.0 to about 6.0 wt % throughout the entire process. With the average sugar concentration reaching about 10.0 wt % or more by continuously adding the biomass, reducing the process time and effectively adjusting the amount of the solvent used, the method is easily put to practical and commercial use.

Finally, in operation S4, the remaining cellulose can be extracted from the biomass, which is a solid component remaining in the reaction vessel after operation S3. At least about 70 wt %, about 80 wt %, or about 85 wt % based on the initial content of the cellulose can remain in the biomass contained in the reaction vessel. Similarly, the cellulose can be directly applied to saccharification and fermentation processes without an additional neutralization process, thereby increasing processability.

A method of fractionating a lignocellulose-based biomass according to another exemplary embodiment can include: providing the lignocellulose-based biomass to a reaction vessel (operation S1); extracting lignin from the biomass by adding aqueous ammonia or a basic solvent to the reaction vessel and transferring the lignin to a first storage tank (operation S2); extracting xylose from the biomass from which the lignin is extracted, by adding an acidic solvent to the reaction vessel, and transferring the xylose to a second storage tank (operation S3); and extracting the remaining cellulose from the biomass, a solid component remaining in the reaction vessel (operation S4).

According to the above-described method, the lignocellulose-based biomass can be continuously processed in a single reaction vessel, and not only the cellulose, a main component of the lignocellulose-based biomass, but also the lignin and the xylose can be fractionated at the same time using a continuous process.

The above-described fractionation process can be performed under milder reaction conditions than those used in conventional methods, for example, at a reaction temperature of about 50 to about 200° C. or about 80 to about 150° C. under a reaction pressure of about 50 to about 330 psig or about 130 to about 320 psig, at a reaction temperature of about 90 to about 180° C. under a reaction pressure of about 140 to about 300 psig, or at a reaction temperature of about 120 to about 160° C. under a reaction pressure of about 150 to about 300 psig. This is because the lignin is extracted from the biomass before the xylose is extracted from the hemicellulose. Excessive degradation of the xylose can be minimized under the mild reaction conditions, thereby increasing the yield of xylose.

Since aqueous ammonia or a basic solvent can be used in operation S2, and an acidic solvent can be used in operation S3, the pH of the reaction vessel in operation S3 can be adjusted to be neutral or weak acidic. Accordingly, lignin and hemicellulose are effectively removed and treated to facilitate enzymatic approach to cellulose, so that the cellulose remaining in the reaction vessel can be directly applied to the fermentation process, and the extracted xylose can also be directly applied to the fermentation process.

After the extraction of the lignin, a washing process can be performed, if desired. In addition, operation S3 can be performed by adding an acid at a high concentration of about 3 to about 8 wt % based on the total weight of the solvent for about 1 to about 10 minutes, and adding an acid at a low concentration of about 0.1 to about 3 wt % based on the total weight of the solvent for about 10 to about 30 minutes.

Solid components remaining in the reaction vessel after the extraction of lignin and hemicellulose contain, as a main component, cellulose. Accordingly, contents of the lignin and hemicellulose remaining in the reaction vessel are minimized, so that almost no saccharification inhibition occurs. In addition, when the cellulose of the solid components is saccharified using an enzymatic process, the efficiency of the enzyme is increased so that the amount of the enzyme used can be greatly reduced compared to the conventional methods. In addition, the reaction rate can be increased, thus improving glucose yield.

2. A Method of Preparing Biofuel

Another exemplary embodiment provides a method of preparing biofuel using xylose and cellulose extracted by fractionating a lignocellulose-based biomass according to the above-described method.

When the lignocellulose-based biomass is fractionated using the above-described method, lignin, xylose and cellulose can be obtained at high yield using a single continuous process.

The biofuel can include alcohol, such as methanol, ethanol or butanol, an alkane-based compound, a $C_3$-$C_6$-based chemical raw material, and an organic acid, but not limited thereto.

For example, the method of preparing biofuel can include a pretreatment process, a saccharification process, a fermentation process, and a separation and purification process. Typically, the fermentation process can include fermenting hexose or pentose contained in the biomass and converting the hexose or pentose into ethanol using yeast, as represented in the following formulae:

$$C_6H_{12}O_6 \rightarrow 2C_2H_5OH + 2CO_2$$

$$3C_5H_{10}O_5 \rightarrow 5C_2H_5OH + 5CO_2$$

In order to obtain ethanol from xylose and pretreated cellulose using the above-described fractionation process, a saccharification process and/or a fermentation process can be performed.

In one example, the biofuel such as ethanol can be obtained by saccharifying and then fermenting the cellulose. The saccharification of the cellulose can be performed using an enzyme, an acid, or a microorganism.

For example, the cellulose can be saccharified using at least one industrial hydrolase selected from the group consisting of α-amylase, glucoamylase, xylanase, cellulase, and a combination thereof, which can hydrolyze starch and (hemi)cellulose into glucose and xylose. Alternatively, the cellulose can be saccharified using diluted sulfuric acid or a microorganism capable of producing the above-described enzymes.

In one example, the production of biofuel can include a saccharification process using enzymes and a fermentation process using a microorganism.

For example, the production of biofuel can include (a) filling a saccharification reaction tank with solid cellulose and a saccharification enzyme and saccharifying the solid cellulose at an optimum temperature for the saccharification enzyme to produce a hydrolyzate; and (b) filling a microorganism fermentation tank with a microorganism and adding the hydrolyzate to the microorganism fermentation tank to ferment the hydrolyzate at an optimum temperature. Or, the production of biofuel can be performed in a simultaneous saccharification and fermentation process in which the both saccharification and fermentation processes are performed at the same time.

In another example, according to the method of the exemplary embodiment, the xylose can be extracted as a monosaccharide, so that it can be directly applied to the fermentation process without a hydrolysis (or saccharification) process to produce the biofuel.

The fermentation process can be performed using a microorganism such as a yeast. For example, the biofuel can be produced by separately culturing a $C_5$ strain and a $C_6$ strain. In some cases, two sugars extracted from the xylose and the cellulose can be mixed and batch-fermented to produce the biofuel.

The fermentation process using the simultaneous saccharification/fermentation strain is a combination of a process of saccharifying cellulose using a commercially available enzyme and a process of preparing ethanol using a strain (refer to M. Takagi, S. Abe, S. Suzuki, G. H. Emert, N. Yata, *Bioconversion symposium proceedings*. IIT, Delhi, pp. 551-557 (1977)). The simultaneous saccharification/fermentation process can reduce the number of reaction vessels used and reduce end-product inhibition by sugar formed in hydrolysis, compared to conventional methods in which a saccharification process is separated from a fermentation process.

3. An Apparatus for Fractionating a Lignocellulose-Based Biomass

Figure 4:
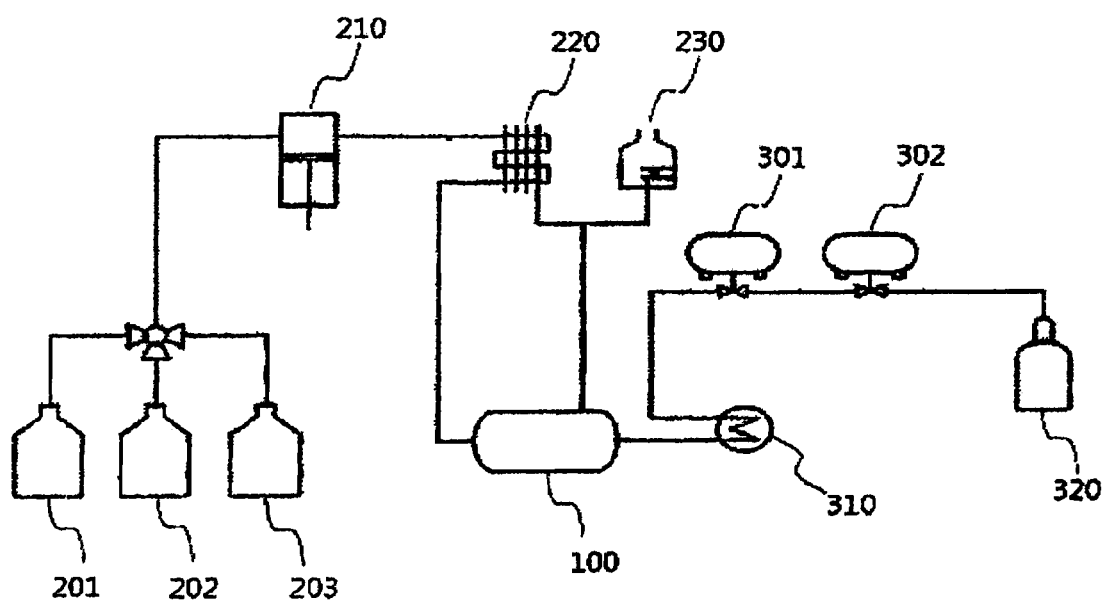
FIG. 4 is a schematic diagram of a fractionation apparatus according to an exemplary embodiment and FIG. 5 is a schematic diagram of a fractionation apparatus according to another exemplary embodiment.

Still another exemplary embodiment provides an apparatus for fractionating a lignocellulose-based biomass. The apparatus will now be described in detail with reference to FIG. 4. FIG. 4 is a schematic diagram of a fractionation apparatus according to another exemplary embodiment of the general inventive concept.

Referring to FIG. 4, the fractionation apparatus according to the present exemplary embodiment includes: a reaction vessel 100; first and second solvent tanks 201 and 202; and a storage tank including first and second storage tanks 301 and 302. The reaction vessel 100 contains a lignocellulose-based biomass. The first and second solvent tanks 201 and 202 can be equipped at one side of the reaction vessel 100 and contain solvents provided to the reaction vessel 100. The first solvent tank 201 contains a first solvent, while the second solvent tank 202 contains a second solvent. The storage tank is equipped at the other side of the reaction vessel 100 and stores extracts from the reaction vessel 100. The storage tank includes the first storage tank 301 storing lignin, and the second storage tank 302 storing xylose.

The fractionation apparatus according to the exemplary embodiment adopts a single reaction vessel 100. Also, the first and second solvents can be continuously added into the fractionation apparatus, by which the lignin and the xylose can be continuously extracted and stored.

Unlike a conventional batch-type apparatus in which only one component of lignocellulose is extracted using a single reaction vessel, the fractionation apparatus according to the exemplary embodiment can separately extract the lignin and xylose from the biomass by continuously adding two kinds of solvents.

In the fractionation apparatus according to the exemplary embodiment, the first and second solvent tanks 201 and 202 can be located at one side of the reaction vessel 100 and contain solvents introduced to the reaction vessel 100. The first solvent tank 201 can contain the first solvent while the second solvent tank 202 contains the second solvent.

The first solvent contained in the first solvent tank 201 can be aqueous ammonia or a basic solvent, and the second solvent contained in the second solvent tank 202 can be an acidic solvent. For example, the basic solvent can be sodium hydroxide (NaOH) or ammonia ($NH_3$), and the acidic solvent can be sulfuric acid ($H_2SO_4$) or any of the basic or acidic compositions described above.

Optionally, the fractionation apparatus can further include a third solvent tank 203 containing water or a buffer solution to adjust the concentration of the solvent or wash the solvent.

Thus, water can be appropriately supplied from the third solvent tank 203 during the addition of the first solvent or the second solvent into the reaction vessel 100 to adjust the concentration of the first solvent or the second solvent.

Optionally, after lignin is extracted by adding the first solvent into the reaction vessel 100, the third solvent tank 203 is open to supply water to the reaction vessel 100, thereby washing the lignin or first solvent remaining in the reaction vessel to remove.

In order to facilitate the addition of solvents into the reaction vessel 100, a solvent pump 210 can be further located between the reaction vessel 100 and the first and second solvent tanks 201 and 202.

Also, a pre-heater 220 and/or a steam generator 230 can be further located between the solvent pump 210 and the reaction vessel 100.

The pre-heater 220 can be coupled to the reaction vessel 100 and can preheat the reaction vessel 100. Alternatively, the pre-heater 220 can be coupled to the solvent pump 210 so that solvents supplied from the solvent tanks 201 and 202 can be preheated before provided to the reaction vessel 100. The pre-heater 220 can be a preheating coil, but not limited thereto.

The steam generator 230 can be used to maintain a reaction temperature of the reaction vessel 100 and can be coupled to the reaction vessel 100 and/or the pre-heater 220. The steam generator 230 can be a steam generator, but not limited thereto.

Meanwhile, the storage tank can be located at the other side of the reaction vessel 100 to receive extracts from the biomass. The storage tank includes the first storage tank 301 storing lignin, and the second storage tank 302 storing xylose.

In order to prevent excessive degradation or transformation of the lignin and xylose extracted from the reaction vessel 100, a cooler and/or heat exchanger 310 can be further located between the reaction vessel 100 and the first and second storage tanks 301 and 302. Thus, the extracted lignin and xylose can be cooled and then transferred to the first and second storage tanks 301 and 302, respectively. The fractionation apparatus can be configured such that heat exchanged by the heat exchanger 320 is utilized by the steam generator 230.

A pressurizer 320 can be coupled to the first and second storage tanks 301 and 302. The pressurizer 320 can be also coupled to the reaction vessel 100, the cooler, or the heat exchanger 310 so that it can provide a constant pressure to maintain a solid-liquid reaction.

In order to maintain a high pressure, a pressure regulator, such as a back pressure regulator or a pressure regulator using nitrogen or compressed air, can be further installed between the storage tanks 301 and 302 and the reaction vessel 100, between the storage tanks 301 and 302 and the cooler/heat exchanger 310, or in the pressurizer 320.

The fractionation apparatus can further include a device for retrieving or circulating the first solvent so that the first solvent can be distilled and recycled for the next reaction after the lignin is extracted.

The fractionation apparatus can further include a third storage tank for storing glucose. After the xylose is fractionated by adding the second solvent, when the second solvent, an acidic solvent, is added again from the second solvent tank 202 into the reaction vessel 100, the pH of the reaction vessel 100 can be changed from neutral to slightly acidic. Here, glucose can be extracted according to temperature and pressure conditions of the reaction vessel 100.

In a variation of the exemplary embodiment, the fractionation apparatus includes a thermometer or pressure gauge installed in each of devices in which respective process operations are performed, in order to maintain a constant reaction temperature and pressure within reaction vessel 100. For example, the thermometer is installed in each of the solvent pump 210, the pre-heater 220, the reaction vessel 100, and the cooler/heat exchanger 310, and the pressure gauge is installed in each of the solvent pump 210 and the pressurizer 320.

An example of a process of fractionating a lignocellulose-based biomass using the fractionation apparatus according to the exemplary embodiments will now be described.

The reaction vessel 100 is filled with the biomass, and steam can be supplied from the steam generator 230 to the pre-heater 220 and the reaction vessel 100 in order to maintain the reaction vessel 100 at a reaction temperature of about 80 to about 150° C. During a rise in the reaction temperature, a predetermined pressure of about 50 to about 300 psig can be applied by the pressurizer 320 before the process operations performed by the solvent pump 210.

Thus, when the reaction vessel 100 is maintained at constant temperature and pressure, the first solvent, such as aqueous ammonia or NaOH solution, is supplied from the first solvent tank 201 via the solvent pump 210 and the pre-heater 220 to the reaction vessel 100 to extract the lignin. After the lignin is extracted, the lignin is transferred to the first storage tank 301 via the cooler/heat exchanger 310.

After lignin extraction for a predetermined process time of about 5 to about 40 minutes, the second solvent, such as $H_2SO_4$, is supplied from the second solvent tank 202 via the solvent pump 210 and the preheater 220 to the reaction vessel 100. Thus, xylose can be fractionated during a neutralization performed by addition of the second solvent for a predetermined time of about 5 to about 20 minutes, and transferred to the second storage tank 302 through the cooler/heat exchanger 310.

After the entire fractionation process is finished, a solid component containing cellulose can remain in the reaction vessel 100. The cellulose can be hydrolyzed by enzymatic saccharification in the reaction vessel or in the continuous process the cellulose is transferred and hydrolyzed in a separate enzymatic saccharification tank.

While the reaction vessel 100 can be a percolation device having the form of a reaction bath, it can have the form of an extruder, which can continuously supply the biomass.

Figure 5:
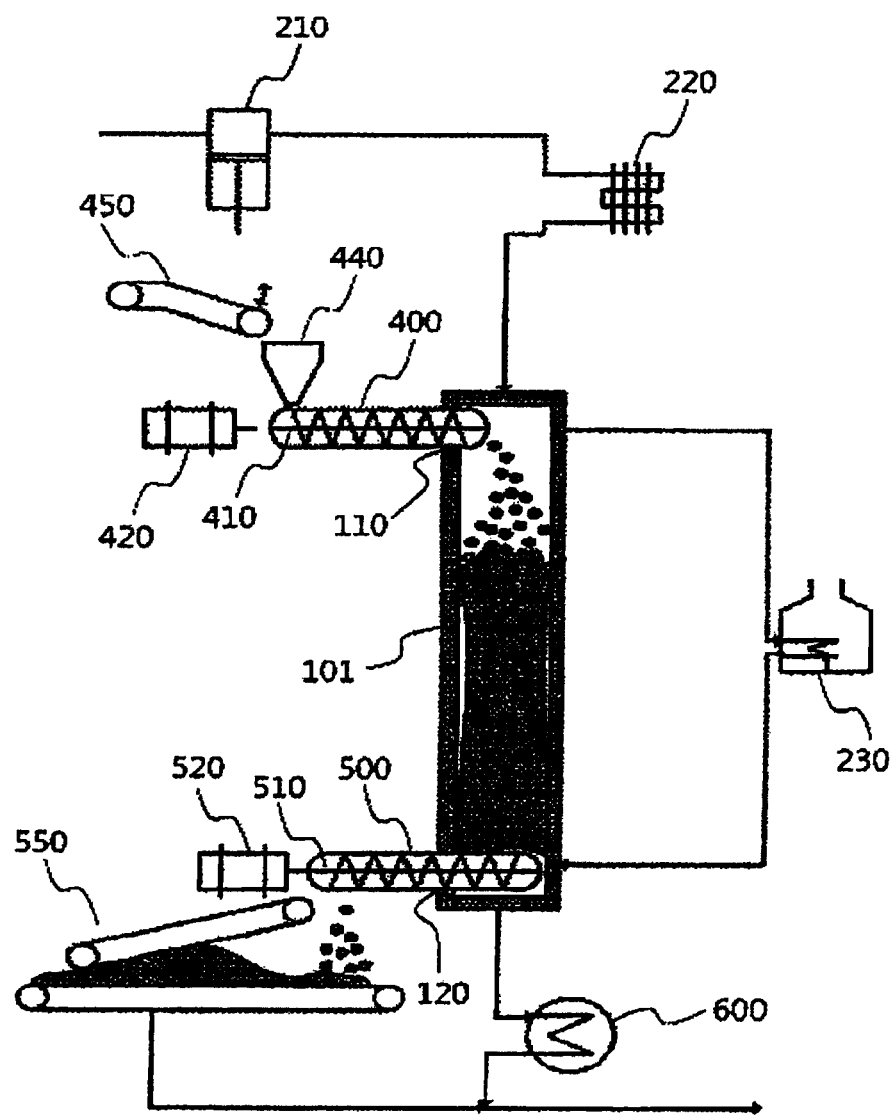

Related thereto, FIG. 5 is a schematic diagram of a reaction vessel 101 of a fractionation apparatus according to another exemplary embodiment. For convenience, the same portions or devices are shown under the same reference numerals as those of FIG. 4.

Referring to FIG. 5, an inlet 110 configured to input the biomass is formed at an upper portion of the reaction vessel 101, and an outlet 120 configured to output the biomass is formed at a lower portion of the reaction vessel 101.

As described above, when the inlet and outlet 110 and 120 are formed the upper or lower portions of the reaction vessel, respectively, the biomass input from the inlet 110 can be transferred to the outlet 120 due to the gravity and the liquid flow without supply of separate power from outside. However, the inventive concept is not limited to the locations of the inlet and outlet 110 and 120.

A screw-type transfer device 400 can be coupled to the inlet 110 to continuously supply the biomass. In addition, a screw-type transfer device 500 can be coupled to the outlet 120 to allow the output biomass to transfer.

Accordingly, a continuous process including providing the biomass, extracting a desired extract from the provided biomass and removing the biomass can be performed.

The transfer devices 400 and 500 can transfer the biomass using axial rotation of screws 410 and 510, respectively, which can be operated by driving forces provided by motors 420 and 520 coupled to the screws 410 and 510.

The biomass provided to the transfer device 400 located at the inlet 110 can be cut by a cutter (not shown) which is coupled to another end of the transfer device. A conveyer belt 450 can also be coupled in order to transfer the biomass to the transfer device 400.

The biomass transferred via the conveyer belt 450 is transferred to the transfer device 400 through a hopper 440 formed at one end of the transfer device, and then input to the reaction vessel.

Meanwhile, the biomass from which lignin and xylose are extracted can be supplied to the transfer device 500 through the outlet 120 to be removed. Here, in order to facilitate the removal of the biomass, a positive pressure can be applied to the inside of the transfer device 500.

In order to separate a liquid component from the biomass during the extraction of the lignin and the xylose, a solid-liquid separator 550 can be coupled to the transfer device 500 coupled to the outlet 120. Accordingly, a liquid polysaccharide or monosaccharide can be separated from the biomass, the solid component.

According to the process of fractionating the biomass in the reaction vessel 101, for example, the biomass is transferred to the hopper 440 via the conveyer belt 450, and supplied to the reaction vessel 101 through the screw-type transfer device 400 located at an upper portion of the reaction vessel 101 to fill the reaction vessel 101. The biomass filling the reaction vessel 101 is heated using a steam generator or an external heat transfer device 230 to reach a predetermined temperature, and then a first solvent is applied to start percolation.

According to the percolation induced by the addition of the first solvent, lignin (about 20 to about 70 wt %) and hemicellulose (about 10 to about 50 wt %) are fractionated in a liquid phase, so that the weight of a remaining solid is reduced to about 30 to about 60 wt % based on the weight of biomass before reaction. Thus, the biomass is transferred to a lower portion of the reaction vessel 101 due to the gravity and liquid flow and packed, so that the volume of the reaction vessel 101 is reduced.

Here, when the biomass is additionally supplied through the transfer device 400 placed at the inlet 110, an empty space in the upper portion of the reaction vessel can be filled again. Third supply of the biomass can be performed, if desired.

After the process time passes, a solvent supply valve (not shown) placed at the upper portion of the reaction vessel 101 is closed, and a liquid exhaustion valve (not shown) placed at the lower portion of the reaction vessel 101 is open, thereby draining a remaining base in the reaction vessel due to an inner pressure to remove a lignin-abundant black liquor.

Afterward, hemicellulose is degraded from the solid biomass in the reaction vessel by percolation using the second solvent, and fractionated into a liquid pentose. After the percolation using the second solvent, the solvent supply valve (not shown) placed at the upper portion of the reaction vessel 101 is closed, and the liquid exhaustion valve (not shown) placed at the lower portion of the reaction vessel 101 is open, thereby removing the second solvent due to an inner pressure.

Finally, the remaining solid biomass can be transferred to the transfer device 500 through the outlet 120 placed at the lower portion of the reaction vessel 101 to be removed.

The reaction vessel 101 can be operated in a completely continuous process including the continuous supply of the biomass, the continuous reaction, and the continuous removal of the remaining solid. In addition, during the extraction of lignin, the biomass can be supplied about 2 to about 5 times larger than the volume of a batch-type reaction vessel. Thus, the yield of pentose such as xylose, which is produced during the extraction of hemicellulose can be increased about 2 to about 5 times.

Hereinafter, examples of the inventive concept will be described in detail.

Example 1

Utilizing the fractionation apparatus shown in FIG. 4, the reaction vessel 100 is filled with a biomass and maintained at a reaction temperature of about 130° C. under a pressure of about 200 psig.

Next, 10% aqueous ammonia is supplied from the first solvent tank 201 to the reaction vessel 100 so that the biomass is percolated for about 5 minutes. Lignin extracted from the biomass is then transferred to the first storage tank 301. About 58 wt % lignin is obtained based on the content of lignin originally present in the biomass.

Next, 3 wt % aqueous $H_2SO_4$ is supplied from the second solvent tank 202 to the reaction vessel 100. After then the extracted xylose is transferred to the second storage tank 302. The yield of the xylose is about 80 wt % based on the content of xylose originally present in the biomass.

Finally, a solid component remaining in the reaction vessel 100 is extracted. The yield of cellulose in the solid component is about 85 wt % based on the content of cellulose originally present in the biomass.

Example 2

A biomass is fractionated in the same manner as in Example 1 except that 10% NaOH is supplied from the first solvent tank 201 to the reaction vessel 100 at a reaction temperature of about 80° C. under a pressure of about 150 psig. The lignin yield is about 65%, the yield of xylose is about 83%, and the yield of cellulose is about 85% as determined above.

Comparative Example 1

Comparative example 1 is prepared as described in the paper entitled "Characterization of Degradation Products from Alkaline Wet Oxidation of Wheat Straw" (Bioresour-Technol. 2002 March; 82(1): 15-26, Klinke, Helene B et al.). Here a biomass is fractionated using the wet oxidation process at a temperature of about 195° C. for about 10 minutes. The yields of cellulose and hemicellulose are shown in Table 1.

Comparative Example 2

Comparative example 2 is prepared as described in the paper entitled "Characterization of Degradation Products from Alkaline Wet Oxidation of Wheat Straw" (Bioresour-Technol. 2002 March; 82(1): 15-26, Klinke, Helene B et. al) and "Characterization of Dilute Acid Pretreatment of Silvergrass for Ethanol Production" (Bioresource Technology 99 (2008) 6046-6053, Klinke, Gia-Luen Guo et al.). Here a biomass is fractionated using an acid process at a temperature of about 121° C. for about 10 to about 180 minutes. The yields of cellulose and hemicellulose are shown in Table 1.

Comparative Example 3

Comparative example 3 is prepared as described in the paper entitled "Ethanol Production from Steam-Explosion Pretreated Wheat Straw" (Applied Biochemistry and Biotechnology 496 Vol. 129-132, 2006; IGNACIO BALLESTEROS et al.). Here a biomass is fractionated using the steam explosion process at a temperature of about 210° C. for about 4 minutes. The yields of cellulose and hemicellulose are shown in Table 1.

Comparative Example 4

A biomass is fractionated using a basic process at a temperature of about 100° C. for about 60 minutes. The yields of cellulose and hemicellulose are shown in Table 1.

Comparative Example 5

Comparative example 5 is prepared as described in the paper entitled "Complete and Efficient Enzymic Hydrolysis of Pretreated Wheat Straw" (Process Biochemistry 37 (2002) 937 to 941; Nicoletta Curreli et al.) and "Comparison of Three Microwave/Chemical Pretreatment Processes for Enzymatic Hydrolysis of Rice Straw" (Biosystems Engineering (2006) 93 (3), 279-283; Shengdong Zhu et al.), a biomass is fractionated. In order to induce the fractionation of the biomass, 2% $H_2SO_4$ is initially supplied for about 2 to about 24 hours to the reaction vessel 100 maintained at a temperature of about 90° C. Next, 1% NaOH is supplied for about 6 to about 24 hours, and 0.3% $H_2O_2$ is then supplied for about 6 to about 24 hours. The yields of cellulose and hemicellulose are shown in Table 1.

Comparative Example 6

Comparative example 6 is prepared as described in the paper entitled "Comparison of Three Microwave/Chemical Pretreatment Processes for Enzymatic Hydrolysis of Rice Straw" (Biosystems Engineering (2006) 93 (3), 279-283; Shengdong Zhu et al.) and "Pretreatment by Microwave/Alkali of Rice Straw and its Enzymic Hydrolysis" (Process Biochemistry, Volume 40, Issue 9, September 2005, Pages 3082-3086; Shengdong Zhu et al.), a biomass is fractionated. In order to induce the fractionation of the biomass, 2% $H_2SO_4$ is initially supplied for about 30 minutes to the reaction vessel 100 maintained at a temperature of about 110° C. Next, 1% NaOH is supplied for about 30 minutes, and 0.3% $H_2O_2$ is supplied for about 12 hours. The yields of cellulose and hemicellulose are shown in Table 1.

Comparative Example 7

In order to fractionate a biomass, a combination of ethanol and water in a ratio of 6:4 is supplied to the reaction vessel 100 at a temperature of about 70° C. for about 4 hours. Thereafter, 2% $H_2O_2$ is supplied at a temperature of about 45° C. for about 16 hours. The yields of cellulose and hemicellulose are shown in Table 1.

lessened, thereby improving process efficiency as compared to conventional methods.

Examples 3 to 10

Utilizing the fractionation apparatus shown in FIG. 4, the reaction vessel 100 is filled with a biomass and maintained under a pressure of about 250 to about 300 psig using nitrogen gas. Under the same process conditions shown in Table 2, 15% aqueous ammonia, as the first solvent, and sulfuric acid, as the second solvent, are sequentially treated. The contents of pentose and furfural, which are contained in the obtained liquid, and pH of the solid biomass finally obtained are measured.

Comparative Example 8

Under the same process conditions shown in Table 2, only aqueous ammonia is applied to pretreat a biomass, and then the contents of pentose and furfural, which are contained in the obtained liquid, and pH of the solid biomass finally obtained are measured.

TABLE 1

|  | Reaction conditions | | | Cellulose | Hemicellulose |
|---|---|---|---|---|---|
|  | Operation 1 | Operation 2 | Operation 3 | Yield rate | Yield rate |
| Ex. 1 | 10% $NH_3$ 130° C./5 min | 3% $H_2SO_4$ 130° C./5 min | — | 85 | 80 |
| Ex. 2 | 10% NaOH 130° C./5 min | 3% $H_2SO_4$ 130° C./5 min | — | 85 | 83 |
| Comp. Ex. 1 | 195° C./10 min | — | — | 65 | 18 |
| Comp. Ex. 2 | 121° C./10-180 min | — | — | 85 | 10 |
| Comp. Ex. 3 | 210° C./4 min | — | — | 65 | 5 |
| Comp. Ex. 4 | 100° C./60 min | — | — | 70 | 11 |
| Comp. Ex. 5 | 2% $H_2SO_4$ 90° C./2-24 h | 1% NaOH 6-24 h | 0.3% $H_2O_2$ 6-24 h | 80 | 13 |
| Comp. Ex. 6 | 2% $H_2SO_4$ 110° C./30 min | 1% NaOH 30 min | 0.3% $H_2O_2$ 12 h | 80 | 3 |
| Comp. Ex. 7 | ethanol-$H_2O$ (6:4) 70° C./4 h | 2% $H_2O_2$ 45° C./16 h | — | 87 | 10 |

Note:
"Comp. Ex." means Comparative Example, and
"Ex." means Example.

As can be clearly seen from Table 1, when a lignocellulose-based biomass is fractionated by supplying two kinds of solvents according to the method of the exemplary embodiments, high yields of cellulose can be obtained, and unexpectedly, high yields of hemicellulose can also be simultaneously obtained. In contrast, the Comparative examples do not give high yields of both hemicellulose and cellulose. Due to the high yields of hemicellulose, the amount of enzyme used can be greatly reduced during enzyme saccharification of the cellulose, and process time and cost can be markedly Comparative Example 9

Under the same process conditions shown in Table 2, only sulfuric acid is applied to pretreat a biomass, and then the contents of pentose and furfural, which are contained in the obtained liquid, and pH of the solid biomass finally obtained are measured.

TABLE 2

|  | Base (%/° C./min/psi) | Washing (° C./min) | Acid (%/° C./min/psi) | Pentose* in Liquid (Retrieval Rate) | Final pH | Furfural** |
|---|---|---|---|---|---|---|
| Ex. 3 | 15/130/20 | — | 1/130/20 | 2% or less | 10 or more | 0.5 g/L or less |
| Ex. 4 | 15/130/20 | — | 3/130/20 | 2% or less | 10 or more | 0.5 g/L or less |
| Ex. 5 | 15/130/20 | — | 5/130/20 | 18.6% | 2 or less | 2.0 g/L |
| Ex. 6 | 15/130/20 | — | 10/130/20 | 2% or less | 2 or less | 2.8 g/L |

TABLE 2-continued

|  | Base (%/° C./min/psi) | Washing (° C./min) | Acid (%/° C./min/psi) | Pentose* in Liquid (Retrieval Rate) | Final pH | Furfural** |
|---|---|---|---|---|---|---|
| Ex. 7 | 15/130/20 | 100/10 | 2/130/20 | 40.7% | 4.8 | 0.5 g/L or less |
| Ex. 8 | 5/130/20 | 100/10 | 2/130/20 | 31.3% | 5.6 | 0.5 g/L or less |
| Ex. 9 | 5/130/20 | 100/10 | 1/130/20 | 32.0% | 6.4 | 0.5 g/L or less |
| Ex. 10 | 15/130/20 | — | 5/130/5 1/130/15 | 42.0% | 4.3 | 0.5 g/L or less |
| Comp. Ex. 8 | 15/130/40 | — | — | — | 10 or more | 0.5 g/L or less |
| Comp. Ex. 9 | — | — | 3/130/40/300 | 2% or less | 2 or less | 3.4 g/L |

*denotes the content of pentose contained in the liquid after pretreatment based on the content of hemicellulose contained in the biomass.
**denotes the detected amount of furfural. When furfural is detected at 0.5 g/L or less, it can be considered not to be substantially detected.

As seen from Table 2, when the biomass is two-step pretreatment using a base and an acid according to the exemplary embodiments, the amount of furfural produced is smaller than that in Comparative example 9 to which only sulfuric acid is treated, and the retrieval rate of pentose in the liquid obtained by degradation of hemicellulose is also very high.

However, after delignification using a base, when the biomass is two-step pretreated using about 1 to about 3% sulfuric acid (Examples 3 and 4), the final pH is about 10 or more, so that the retrieval rate of pentose in the liquid is about 2% or less. It is estimated that since most of the sulfuric acid supplied thereto is neutralized by a remaining base, the hemicellulose is not degraded into a pentose but present in the form of an oligomer.

Meanwhile, when high concentration sulfuric acid is added after the pretreatment using a base (Examples 5 and 6), the retrieval rate of pentose is high, but the final pH is about 2 or less, so that it can be seen that the amount of furfural produced is relatively high. It is because the remaining base in the reaction vessel is neutralized by an acid supplied at an early stage, and then the reaction vessel is under an acidic condition, so that the some pentose are retrieved, but they are excessively degraded and converted into furfural due to high acidity.

Thus, it can be concluded that, in the two-step pretreatment, the appropriate final pH ranges from about 2 to about 10, or from about 4 to about 7.

After a first base treatment, when a process temperature is decreased to 100° C. or less and then a post-treatment is performed after a washing process using water (Examples 7 to 9), pentose retrieved from the liquid is obtained very high, e.g., about 30% or more. This is because hemicellulose is efficiently degraded since desired final pH is achieved by adding only a low concentration acid by removing almost all reaming base from the reaction vessel.

Particularly, when the biomass is percolated using 2% acid after the 15% base treatment and the washing process with water (Example 7), the retrieval rate of the liquid pentose is about 40.7%. In addition, when the remaining solid biomass is enzymatic-sacchariﬁed, the retrieval rate of the pentose is about 35%, and thus it can be confirmed that total 75.7% of pentose are retrieved from the liquid and the solid residue.

In addition, when an acid is supplied at a concentration of 5% or more to neutralize the biomass without the washing process after the base treatment, and then an acid is added at a low concentration of about 1 to about 2% (Example 10), it can be seen that the retrieval rate of the pentose is about 42%, and the amount of furfural produced is also small.

A method and apparatus for fractionating a lignocellulose-based biomass according to exemplary embodiments can prevent excessive degradation of xylose by sequentially extracting lignin and xylose, and have excellent processibility due to a continuous process. Moreover, the method and apparatus can greatly reduce energy and operating costs, so that it can have industrial efficiency.

While exemplary embodiments have been disclosed herein, it should be understood that other variations may be possible. Such variations are not to be regarded as a departure from the spirit and scope of exemplary embodiments of the present application, and all such modifications as would be obvious to one skilled in the art are intended to be included within the scope of the following claims.

What is claimed is:

1. A method of continuously fractionating a lignocellulose-based biomass, comprising:
    providing the lignocellulose-based biomass in a reaction vessel at a pressure of about 130 to about 320 psig;
    extracting lignin from the biomass by adding a first solvent capable of dissolving the lignin, and wherein the first solvent is added to the reaction vessel for about 5 to about 40 minutes, at a temperature of about 80 to about 150° C.;
    extracting xylose by adding an acid at a high concentration of about 3 to about 8 wt % based on the total weight of the solvent for about 1 to about 10 minutes, and adding an acid at a low concentration of about 0.1 to about 3 wt % based on the total weight of the solvent for about 10 to about 30 minutes; and
    extracting the remaining cellulose from the biomass from which the lignin and the xylose are extracted,
    wherein the method is performed without removing the first solvent by washing between the lignin extraction and the xylose extraction steps.

2. The method according to claim 1, wherein the extracting of the lignin from the biomass is followed by evaporating and recycling the first solvent.

3. The method according to claim 1, wherein the first solvent is aqueous ammonia or a basic solvent.

4. The method according to claim 3, wherein the basic solvent is utilized and includes at least one selected from the group consisting of sodium hydroxide (NaOH), calcium hydroxide (Ca(OH)$_2$), sodium sulfide (Na$_2$S), potassium hydroxide (KOH) and combinations thereof.

5. The method according to claim 3, wherein the concentration of the aqueous ammonia ranges from about 2.5 to about 15 wt % ammonia based on the total weight of the solvent, and the concentration of the basic solvent ranges from about 5 to about 10 wt % based on the total weight of the solvent.

6. The method according to claim 1, wherein the acid includes at least one selected from the group consisting of sulfuric acid (H$_2$SO$_4$), hydrochloric acid (HCl), phosphoric acid (H$_3$PO$_4$), nitric acid (HNO$_3$), peracidic acid and combinations thereof.

7. The method according to claim 1, wherein after extracting the xylose, the pH of the biomass is adjusted to about 4 to about 6.

8. The method according to claim 1, wherein the extracted lignin is subjected to a cooling process or a heat exchange process and then stored in a first storage tank, and the extracted xylose is subjected to a cooling process or a heat exchange process and then stored in a second storage tank.

9. The method according to claim 1, wherein the yield of the extracted lignin is about 50% or more based on the content of lignin present in the original biomass, the yield of the extracted xylose is about 80% or more based on the content of xylose present in the original biomass, and the yield of the extracted cellulose is about 85% or more based on the content of cellulose present in the original biomass.

10. The method according to claim 1, wherein an extract obtained by extracting the xylose contains total 3 g/L or less of furfural and hydroxymethylfurfural (HMF).

\* \* \* \* \*